United States Patent
Eglise (10) Patent No.: US 6,579,498 B1
(45) Date of Patent: Jun. 17, 2003

(54) IMPLANTABLE BLOOD GLUCOSE SENSOR SYSTEM

(76) Inventor: David Eglise, Snowdrop Villas, 53 Alma Road, Windsor, Berkshire SL4 3HH (GB)

( * ) Notice: Subject to any disclaimer, the term of this patent is extended or adjusted under 35 U.S.C. 154(b) by 0 days.

(21) Appl. No.: 09/673,094
(22) PCT Filed: Mar. 22, 2000
(86) PCT No.: PCT/GB99/00900
§ 371 (c)(1), (2), (4) Date: Oct. 11, 2000
(87) PCT Pub. No.: WO99/48419
PCT Pub. Date: Sep. 30, 1999

(30) Foreign Application Priority Data

Mar. 20, 1998 (GB) .............................. 9805896

(51) Int. Cl.⁷ .............................................. G01N 21/29
(52) U.S. Cl. ............................... 422/82.05; 422/82.08; 436/172
(58) Field of Search ................ 436/20, 172; 422/82.05, 422/82.08; 600/341, 310, 347, 346

(56) References Cited

U.S. PATENT DOCUMENTS

| | | | |
|---|---|---|---|
| 4,172,459 A | 10/1979 | Hepp | 128/697 |
| 4,436,094 A | 3/1984 | Cerami | 128/635 |
| 4,538,616 A | 9/1985 | Rogoff | 128/632 |
| 4,822,336 A | 4/1989 | DiTraglia | 604/50 |
| 5,308,967 A | 5/1994 | Jurisch | 235/492 |
| 5,337,747 A | 8/1994 | Neftel | 128/635 |
| 5,372,133 A * | 12/1994 | Hogen Esch | 128/631 |
| 5,519,729 A | 5/1996 | Jurisch et al. | 375/259 |
| 5,545,567 A * | 8/1996 | Gretillat et al. | 436/172 |
| 5,597,534 A | 1/1997 | Kaiser | 422/82.02 |
| 5,628,310 A * | 5/1997 | Rao et al. | 128/633 |
| 5,704,352 A | 1/1998 | Tremblay et al. | 128/630 |
| 5,871,698 A | 2/1999 | Laguna et al. | 422/82.05 |
| 6,268,161 B1 | 7/2001 | Han et al. | |

FOREIGN PATENT DOCUMENTS

| | | |
|---|---|---|
| DE | 42 03 466 A1 | 8/1993 |
| EP | 0 554 955 A1 | 8/1993 |
| EP | 0 685 730 A1 | 12/1995 |
| GB | 2 335 743 A | 9/1999 |
| WO | 91/01680 | 2/1991 |
| WO | 93/13803 | 7/1993 |
| WO | 94/25105 | 11/1994 |
| WO | 96/36275 | 11/1996 |
| WO | 97/33513 | 9/1997 |

* cited by examiner

Primary Examiner—Jill Warden
Assistant Examiner—Sam Siefke
(74) Attorney, Agent, or Firm—Davis & Bujold, P.L.L.C.

(57) ABSTRACT

An implanted sensing device (1) for monitoring an analyte (e.g. blood-glucose) includes a non-toxic macromolecular material (2) encapsulated within an envelope (3) of biocompatible semi-permeable membrane. A sensor (4) responds to change of a physical property (e.g. viscosity) of the material (2) when the analyte contacts the material (2), to signal the change to a measurement circuit (5) that together with the sensor (4) and a transponder (6) are included within the envelope (3). The transponder (6) is interrogated externally of the implanted sensor (1) by an interrogation unit (7) to transmit measurement data for processing and storage. The interrogation signal is utilized within the device (1) to power the circuit (5) and transponder (6) and conveys data to the device for re-calibration or resetting of signal-datum values to compensate for aging or drift.

19 Claims, 8 Drawing Sheets

IMPLANTABLE BLOOD GLUCOSE SENSOR SYSTEM

BACKGROUND OF THE INVENTION

This invention relates to sensing devices and systems, and is particularly concerned with sensing devices and systems for use in monitoring the presence or activity of specific chemical analytes.

SUMMARY OF THE INVENTION

According to one aspect of the present invention a sensing device for use in monitoring the presence or activity of a specific chemical analyte, comprises an enclosure having a membrane-wall that is semi-permeable to said chemical analyte, macromolecular material contained within the enclosure, said material exhibiting physical change in response to contact with said chemical analyte, a sensor contained within the enclosure to respond to said physical change, and means for transmitting a signal from said sensing device dependent on the response of said sensor.

The sensing device according to the invention is especially applicable for monitoring the presence or level of activity of a specific bio-chemical, drug or other analyte in vivo, within the body of a human or animal patient. In this context the sensing device may be provided for implant subcutaneously or otherwise within the patient so that the particular analyte can be sensed as it permeates the semi-permeable wall of the device.

The said material may be such as to exhibit change in a Theological parameter thereof in response to the analyte. The parameter may be viscosity, and the material, which may be for example a mixture of concanavalin A and ficoll, may be responsive to the presence of glucose to exhibit a change of its viscosity or other parameter. In the context of response to glucose, the sensing device of the invention has particular application for in vivo monitoring of the blood-glucose of diabetic patients.

The means for transmitting a signal from the sensing device of the invention may be contained within said enclosure, and said enclosure may be in the form of a capsule wholly or substantially wholly of semi-permeable membrane. Moreover, the means for transmitting a signal from the sensing device may include means for deriving digital data in accordance with the response of the sensor and for transmitting this from said sensing device.

According to another aspect of the present invention a sensing system for use in monitoring the presence or activity of a specific chemical analyte, comprises a sensing device and interrogating means that is operable for interrogating said sensing device, said sensing device comprising an enclosure having a membrane-wall that is semi-permeable to said chemical analyte, macromolecular material contained within the enclosure, said, material exhibiting physical change in response to contact with said chemical analyte, a sensor contained within the enclosure to respond to said physical change, and means operable in response to interrogation of said sensing means by said interrogating means for transmitting a signal dependent on the response of said sensor, to said interrogating means.

The signal dependent on the response of said sensor may be transmitted to said interrogating means by electromagnetic-wave transmission. Similarly, interrogation of said sensing means may be effected by electromagnetic-wave transmission from said interrogating means. In this latter case, electrical power for the means operable in response to interrogation of said sensing means, may be derived from the electromagnetic-wave interrogating transmission.

BRIEF DESCRIPTION OF THE DRAWINGS

A sensing system, and sensing devices for use therein, all according to the present invention will now be described, by way of example, with reference to the accompanying drawings, in which.

DESCRIPTION OF THE PREFERRED EMBODIMENTS

The sensing system to be described is for use for in vivo monitoring of the presence or level of activity of a specific bio-chemical, drug or other analyte within a patient.

Figure 1:
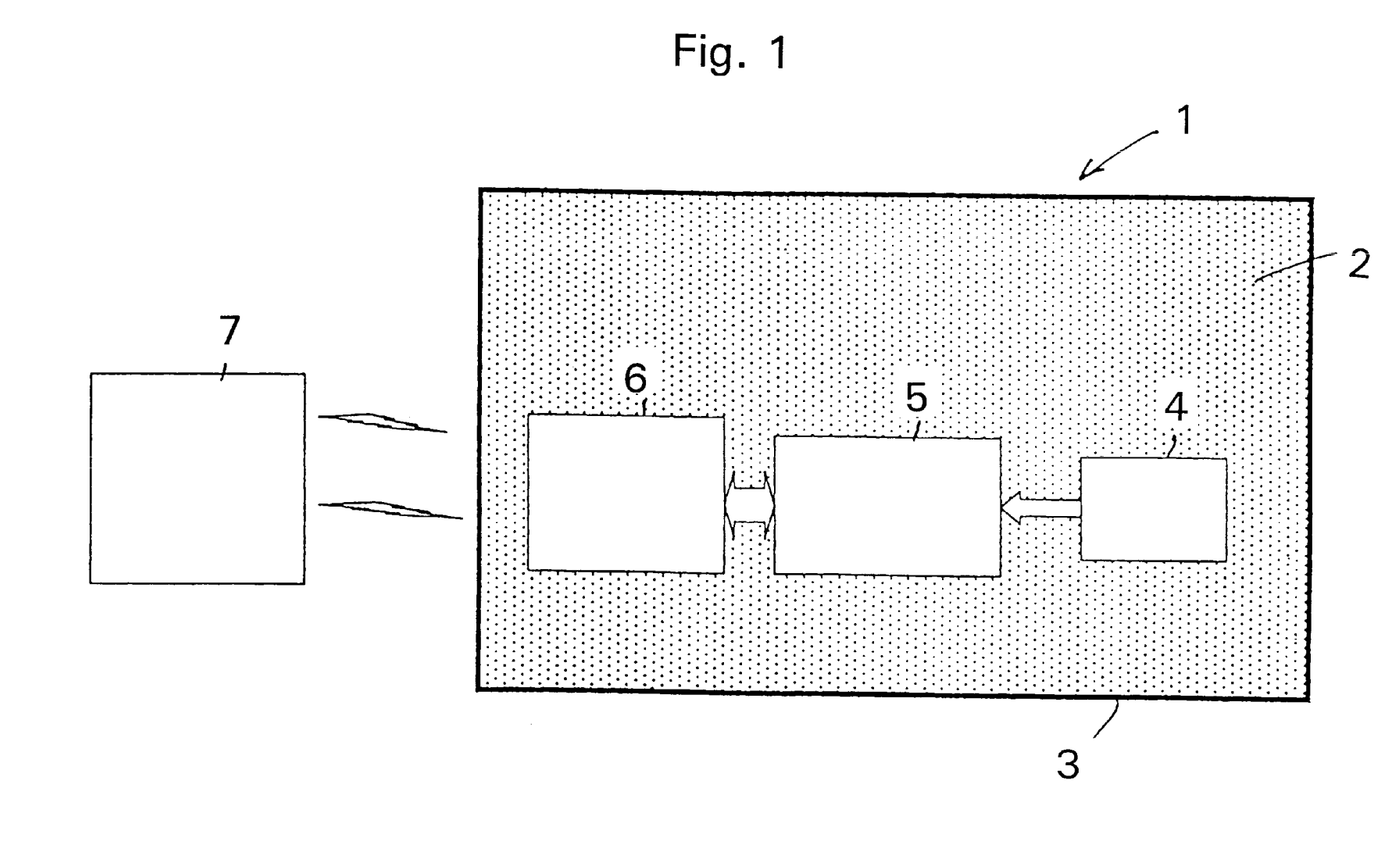
FIG. 1 is a block schematic diagram illustrating the sensing system according to the present invention.

Referring to FIG. 1, the sensing system includes a sensing device 1 that is implanted subcutaneously in the patient. The sensing device 1 includes a non-toxic macromolecular mixture or compound 2 encapsulated within an envelope 3 of bio-compatible semi-permeable membrane. The mixture or compound 2 has the characteristic that its physical properties change when it is in the presence of the relevant analyte, and the change in the physical condition of the mixture or compound 2 that in this respect takes place when the analyte permeates the wall of the envelope 3 is sensed by a sensor 4. The sensor 4 is encapsulated with the mixture or compound 2 within the envelope 3, and supplies an electric signal dependent on the sensed physical-change to a measurement circuit 5.

The circuit 5, like the device 4, is encapsulated with the mixture or compound 2 within the envelope 3, and from the signal supplied by the sensor 4 derives a digital-data signal that provides a measure of the physical condition of the mixture or compound 2 sensed. This signal is supplied to a radio-frequency transponder 6 which is also encapsulated with the mixture or compound 2 within the envelope 3.

The transponder 6 is interrogated externally of the implanted sensing device 1 by actuation of an interrogation unit 7. The measurement data derived by the circuit 5 is in consequence transmitted from the transponder 6 and this data as received by the unit 7 is either processed and stored within the unit 7 locally, or communicated to a data-acquisition system (not shown). The activity of the chemical analyte within the patient can be determined from the measurement data received from the sensing device 1 and can thus be continually or periodically monitored by the system of the invention. Moreover, suitable alarm and/or other action (for example, administration of a drug) can be taken when the activity of the analyte makes this desirable or necessary in the context of the monitoring operation.

The sensing device of the invention has particular application in the monitoring of blood-glucose in diabetic patients. Attempts have been made to develop an in vivo glucose sensor for this purpose, focused on adapting known biosensor-technology. But these attempts have been largely frustrated by problems of bio-compatibility, drift, instability, fouling, infection and electrical interconnection with the implant. However, the principal problems arise from the inherent instability of any enzyme-based system which limits the potential life of the sensing device and the design of a reliable interface between the indwelling sensing device and its associated, external electronics. These problems can be to overcome to a major extent with the sensing system of the present invention in that the enclosure may be biocompatible and contain a non-toxic macromolecular mixture or compound responsive by physical rather than biochemical change to the blood-glucose level of the patient. The physical response of the macromolecular mixture or compound is reversible so that the sensing device can have a very long operational life.

Although described.above as utilised as an implant, the sensing device may be used in other contexts where it is desirable or necessary to provide for monitoring the presence or activity of a specific chemical, using self-contained sensing without the necessity for external electrical or other connection with the sensing device.

The mixture or compound 2 has an important role in the sensing system and device of the invention in that it exhibits a physical change in response to the analyte that is being monitored. By way of example, the material 2 may be a mixture of concanavalin A and ficoll which exhibits a rheological change to glucose. Other suitable mixtures or compounds may be used, and for longevity and optimum performance may be custom synthesised using moleculardesign or molecular-imprinting methods. The involvement of non-proteinaceous synthetic recognition molecules may be found preferable.

The physical change of the mixture or compound 2 sensed by the sensor 4 within the sensing device 1 may, as indicated above, be rheological, and may be specifically change of viscosity. By way of alternative, the physical change sensed may be related to electrical conductivity, density, volume, pressure or luminosity or fluorescence. Luminosity or fluorescence may be sensed by the sensor 4 during stimulation of the mixture or compound 2 by visible or non-visible light incident on the device 1 from an externally-located laser. A similar stimulation of a sensed physical property may be achieved using acoustic radiation.

The semi-permeable envelope 3 may be fabricated of metallic, semi-synthetic or natural materials, examples of which are sintered titanium, polyvinyl chloride, silicone rubber, nylon and cellulose derivatives. For in vivo applications of the sensing device 1, the membrane is desirably treated with a chemical such as phosphoryl choline, or derivatives, to minimize cell or protein adhesion.

Figure 2:
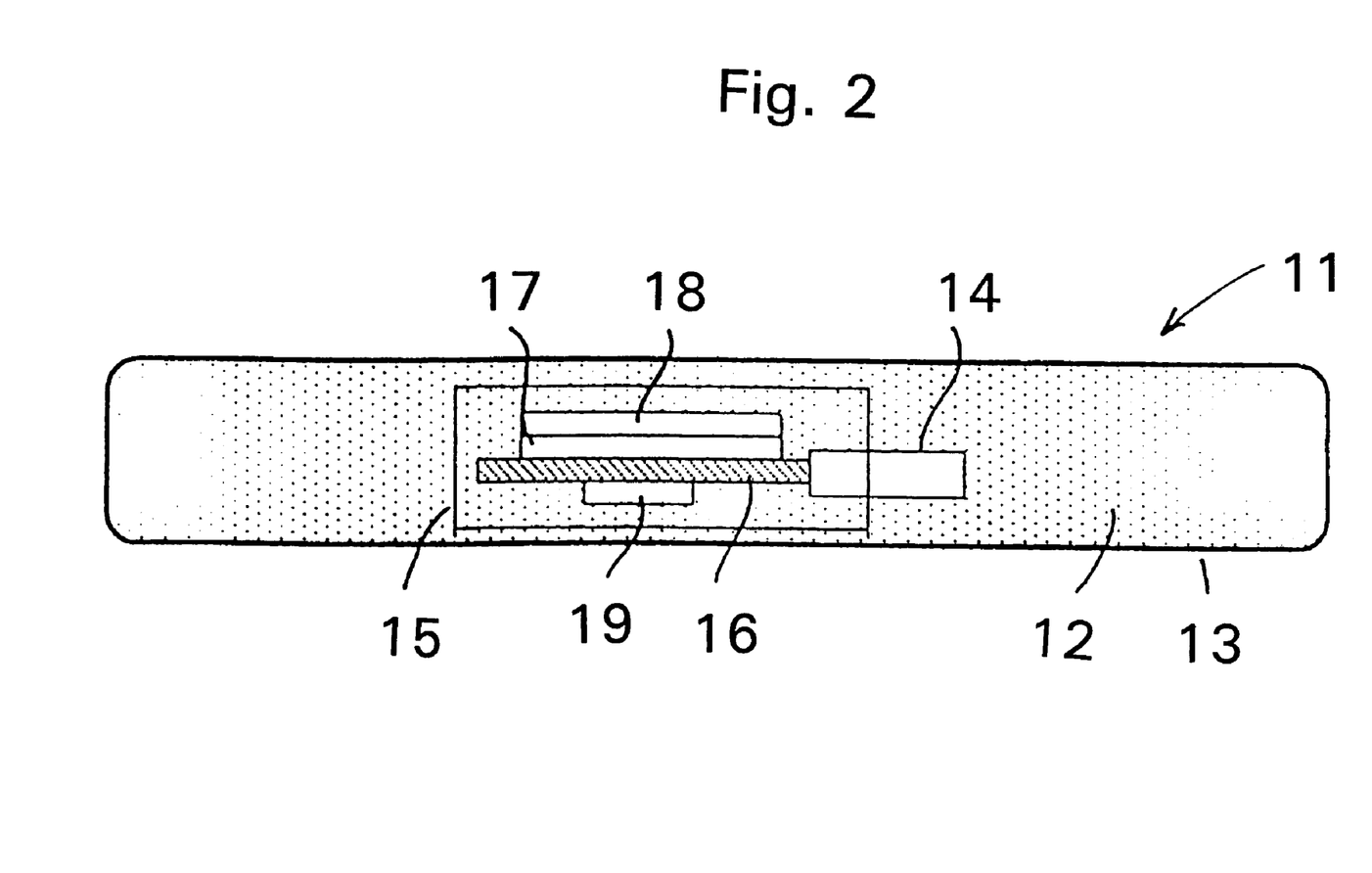
FIG. 2 is a sectional view of a sensing device according to the invention, that forms part of the system of FIG. 1.

The sensing system of FIG. 1 may be used specifically for monitoring blood-glucose levels in a patient suffering from diabetes, and the sensing device of the system may then take the form shown in FIG. 2.

Referring to FIG. 2, the sensing device in this case has the form of a thin capsule 11 containing for example a mixture of concanavalin A and ficoll, as the macromolecular material 12. The mixture or compound 12 is encapsulated within a continuous, seamless wall 13 formed wholly or substantially wholly of semi-permeable membrane. A sensor 14 immersed in the mixture or compound 12 within the capsule 11 is connected through the wall of an environmental housing 15 that contains the electronic circuitry of the sensing device 11. In particular, the housing 15 incorporates a substrate 16 to which the sensor 14 is coupled and which carries measurement and transponder circuitry 17 together with the transponder antenna 18 and a charge-storage capacitor 19.

The capsule 11 is implanted subcutaneously in a patient to respond to change in his/her blood-glucose level. The change of viscosity that occurs in the mixture or compound 12 in response to the change in glucose level permeating the semi-permeable wall 13, is sensed by the sensor 14 and communicated to the circuitry 17. In particular, for a concanavalin A—ficoll mixture a large change in viscosity (for example, 1 to 10 mM) is exhibited between the minimum and maximum levels of a patient's blood-glucose level. The output of the sensor 14 in response to the change is translated within the circuitry 17 into data representative of viscosity and, correspondingly, of the blood-glucose level, for transmission to the appropriate interrogation unit via the antenna 18.

The sensor 14 in this example may be of a kind which in response to change of viscosity of the mixture or compound 12, exhibits a change of piezo-mechanical coupling efficiency. This change can be used to create a voltage or phase change in an applied signal. In the case in which phasechange is utilised, the circuitry 17 may take the form illustrated in FIG. 3.

Figure 3:
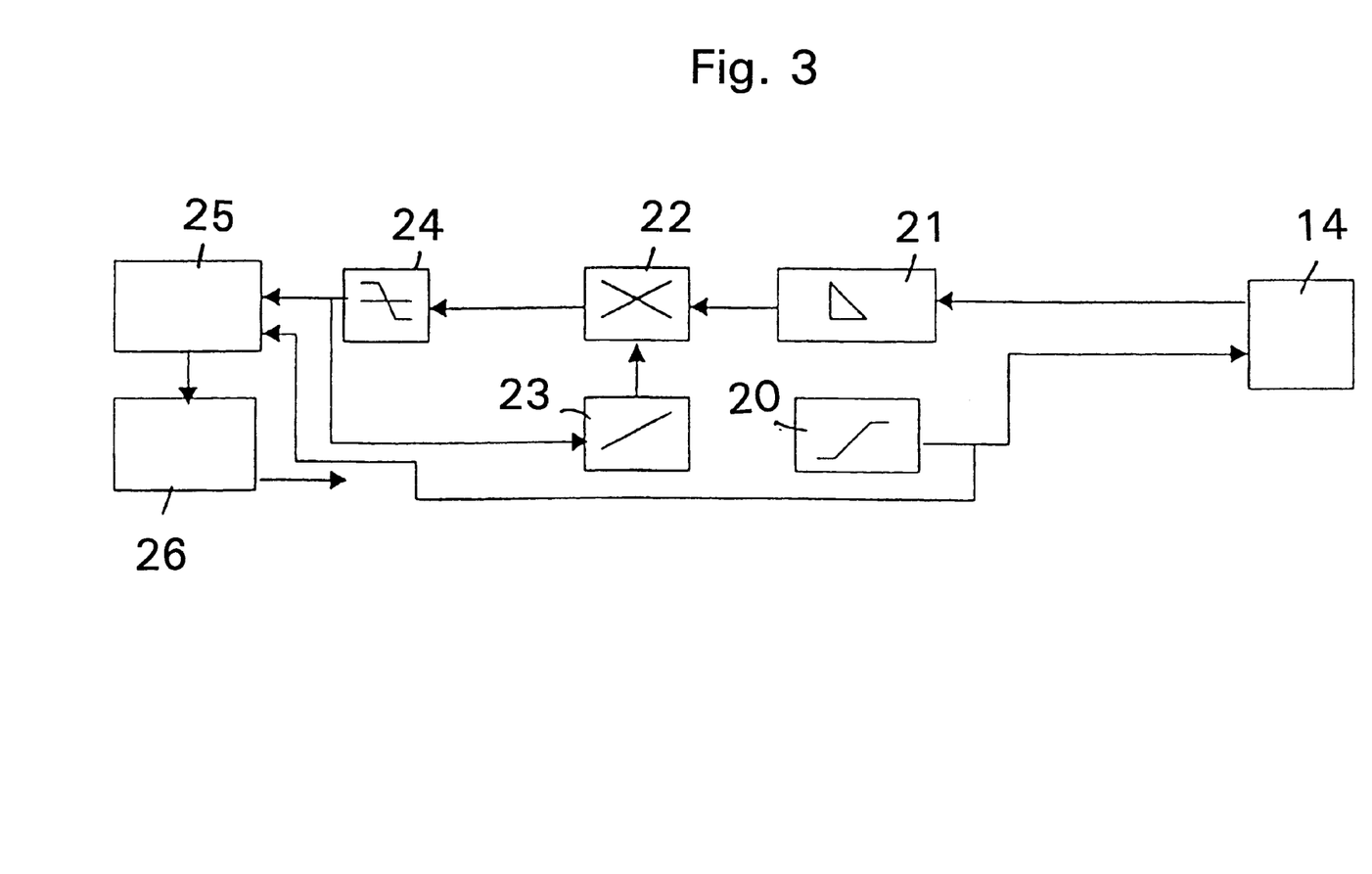
FIG. 3 is a block-schematic representation of the electrical circuitry of the sensing device of FIG. 2.

Referring to FIG. 3, an oscillatory waveform is applied to the sensor 14 from an oscillator 20, and the output signal of the sensor 14 is supplied via a voltage-buffer stage 21 to a phase detector 22 for comparison with the output of a voltage-controlled oscillator 23 in a phase-locked loop that includes a loop-filter 24. The resultant output signal of the filter 24 is supplied with the output signal of the oscillator 20 to a signal processor 25 to derive the relevant data from the detected phase shift between the two signals, and to supply this to a transponder circuit 26.

Electrical energy to power the electronics of the capsule 11 is derived within the transponder circuit 26 without the need for the capsule 11 to include a battery. The required power is derived from the interrogation signal transmitted from the interrogation unit 7 (FIG. 1). This signal received via the antenna 18 charges the storage capacitor 19 and it is from this charge that the circuitry 17 is powered to gather the blood-glucose measurement data and transmit it via the antenna 18 for external use.

In an alternative construction of the capsule 11, the sensor 14 used is of a form that utilises the transmission of acoustic waves within the mixture or compound 12. The form of sensor 14 and circuitry 17 used in this case is shown in FIG. 4 and will now be described.

Figure 4:
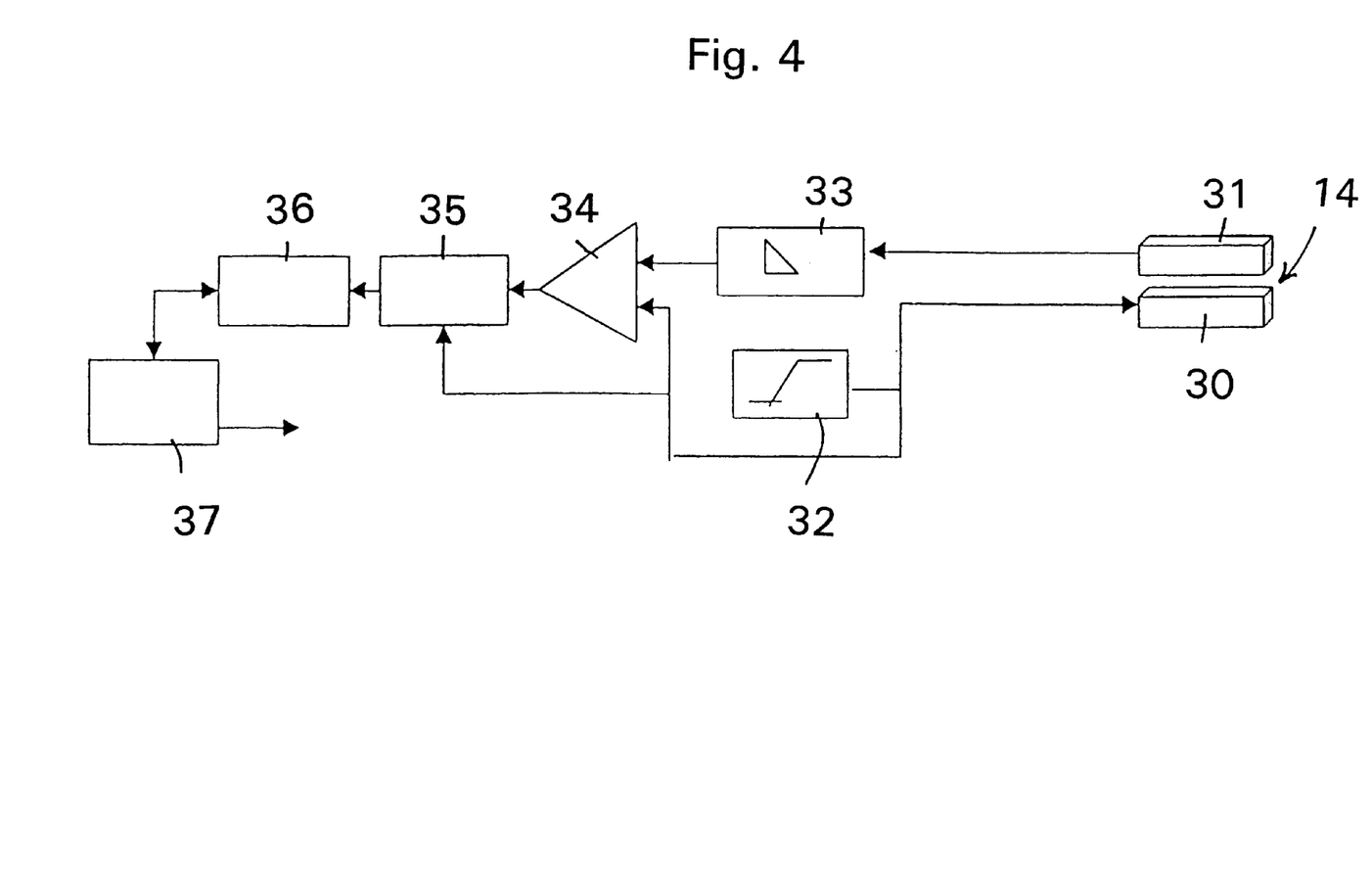
FIG. 4 is a block-schematic representation of electrical circuitry that may be used as an alternative to the electrical circuitry of FIG. 3 for the sensing device of FIG. 2.

Referring to FIG. 4, the sensor 14 in this case comprises spaced piezoelectric transducer elements 30 and 31 immersed in the mixture or compound 12. The element 30 is energised from an oscillator 32 and the consequent vibrations transmitted via the mixture or compound 12 are detected by the element 31. The resultant signal derived by the element 31, which can be readily correlated in amplitude and frequency with viscosity of the mixture or compound 12, is applied via a voltage buffer stage 33 for comparison with the output signal of the oscillator 32, in a comparator 34. The output signal of the comparator 34 is utilised within a processor 35 to derive in relation to the output signal of the oscillator 32, the desired measurement data for indicating blood-glucose level. Data stored in a non-volatile memory 36 sets the datum value against which the measurement data is derived for transmission by a transponder circuit 37.

Figure 5:
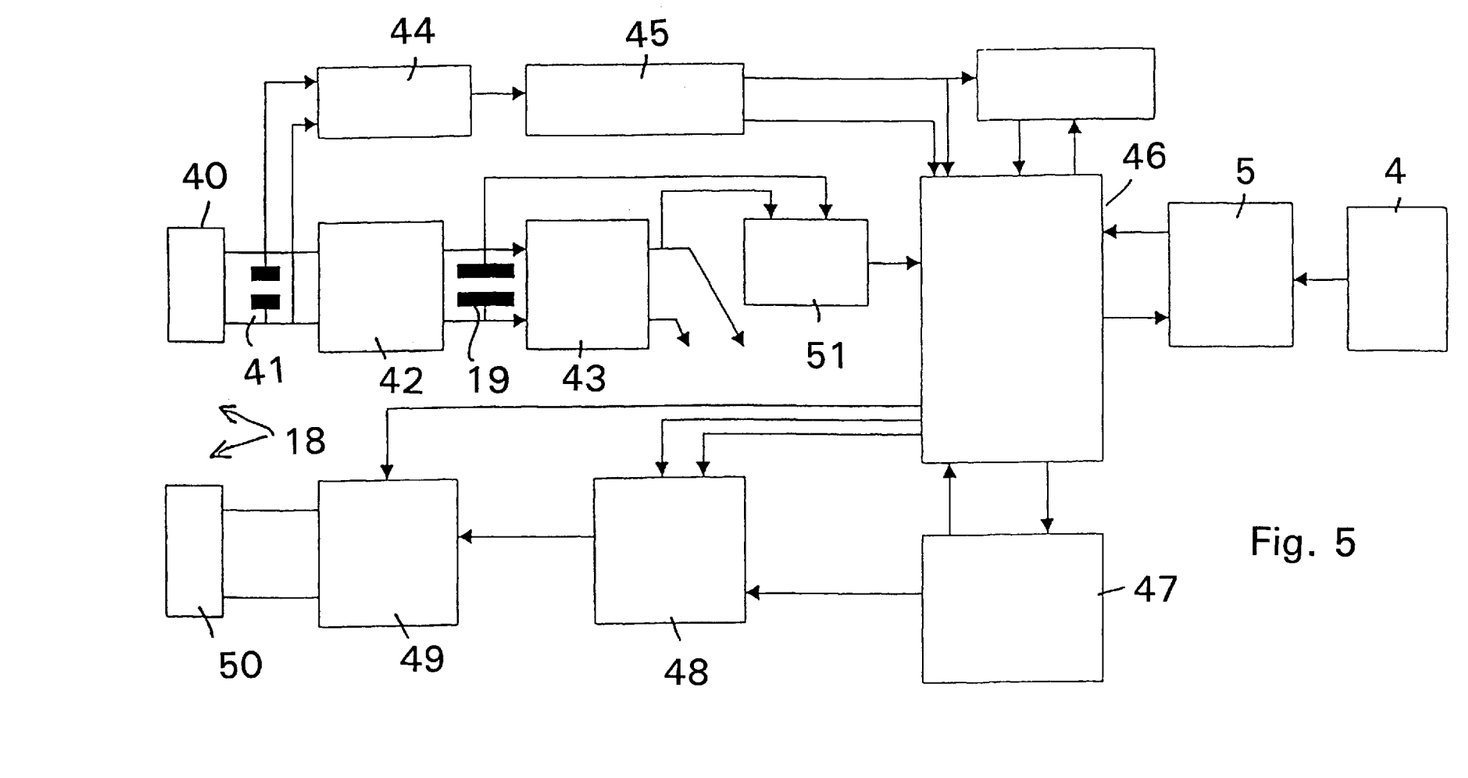
FIG. 5 provides a block-schematic representation of the electrical circuitry of a transponder of the sensing device of FIG. 2.

The transponder 6 of FIG. 1 (or specifically the transponder units 26 and 37 of FIGS. 3 and 4 respectively) may be constructed as illustrated in FIG. 5.

Referring to FIG. 5, the radio-frequency interrogation signal is received in the antenna 18 within a resonant circuit that is formed by an antenna coil 40 with shunt capacitor 41. The oscillatory output across the coil 40 is supplied via a rectifier 42 to charge the storage capacitor 19 in providing electrical power to the electronics of the capsule 11 via a regulator 43, and is also supplied via a comparator 44 to a demodulator 45. The demodulator 45 derives data that is transmitted to the transponder 18 in the interrogation signal, and supplies this to a processor unit 46. This data is used within the processor unit 46 for protocol synchronisation and to set and/or re-set datum levels for the measurement data signalled by the measurement circuit 5 from the sensor 4 (FIG. 1).

The data derived by the processor unit 46 is stored in a memory 47. This stored data is read out and under control of the processor unit 46 is combined with other data in a MUX unit 48 for transmission via a modulator 49 and coil 50 of the antenna 18. Transmission is controlled by the processor unit 46 in dependence upon power-supply operation as determined by a power on/reset unit 51.

Figure 6:
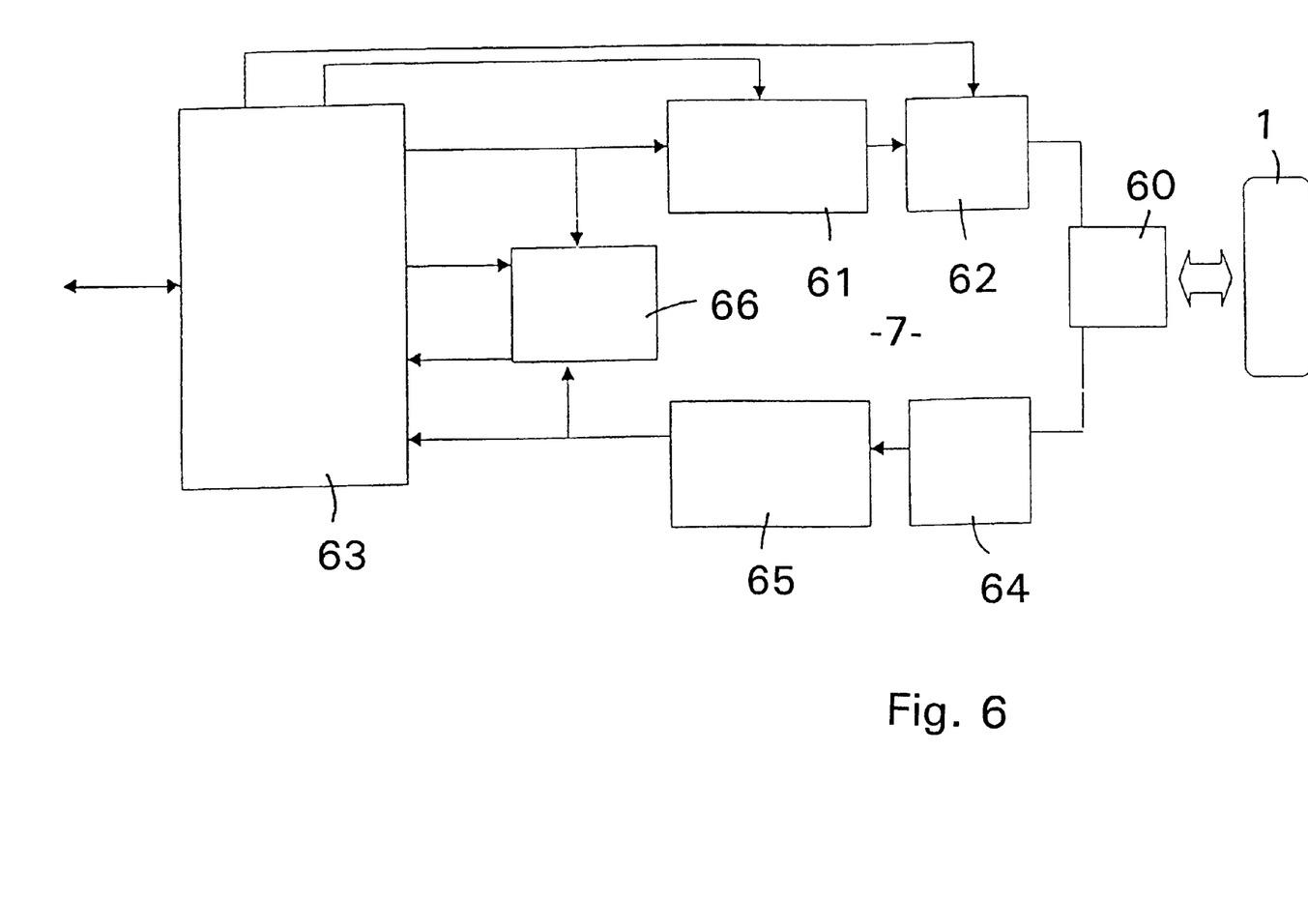
FIG. 6 provides a block-schematic representation of the electrical circuitry of an interrogator unit that forms part of the sensing system of FIG. 1.

The interrogation unit 7 of the system of FIG. 1 may be as illustrated in FIG. 6.

Referring to FIG. 6, the transmission of the interrogation signal to the sensing device 1 is effected via an antenna 60 that is supplied with the signal from a modulator 61 via a power-amplifier 62. The modulator 61 modulates the transmitted radio-frequency signal with data that is derived from a control unit 63 that includes digital storage. This data is derived within the unit 63 or within a data-acquisition station (not shown) to which it may be connected, in dependence upon the data that is to be transmitted by the sensing device 1 and the datum levels to which measurement is to be carried out therein.

The data signals received by the antenna 60 from the sensing device 1 are amplified in an amplifier 64 and demodulated in a demodulator 65 for supply to the unit 63. A comparator 66 is active to derive control input signals for the unit 63 dependent upon the transmitted and received signals.

The interrogation unit 7 of FIG. 1 may be implemented in the form of a unit that is worn on the wrist in the manner of a wristwatch. This is illustrated in FIG. 7 where a capsule 70 of the same form as capsule 11 of FIG. 2 is to be understood as having been implanted subcutaneously in the wrist of a patient, and the interrogation unit 71 in this case has straps 72 for holding it to the wrist immediately over the implanted capsule 70.

Figure 7:
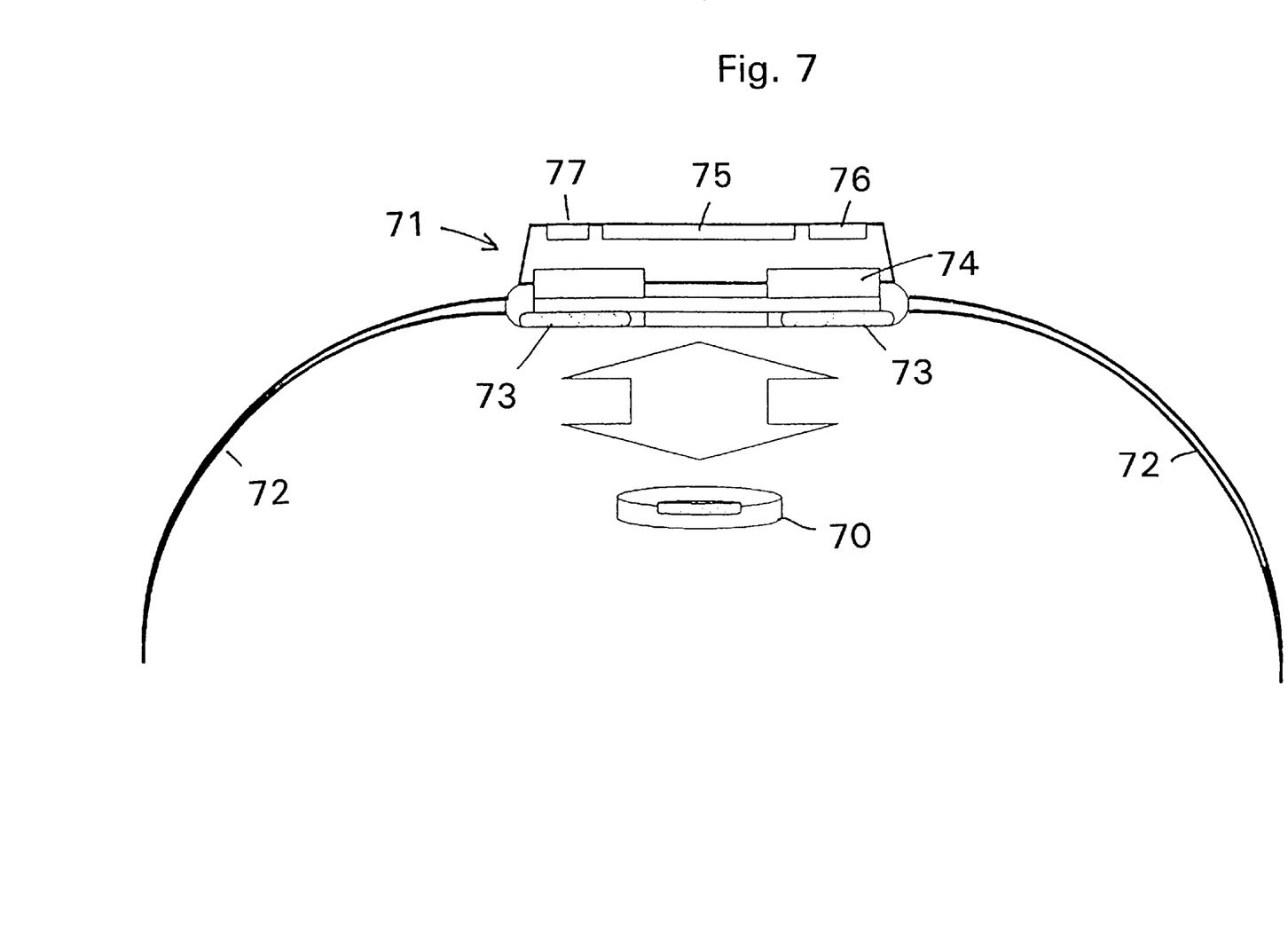
FIG. 7 is illustrative of a practical implementation of the sensing system of FIG. 1.

Referring to FIG. 7, an antenna coil 73 is incorporated in the base of the unit 71 beneath the associated electronic circuitry 74. The unit 71 also incorporates an LCD display 75 and an audible-alarm facility 76 together with pushbuttons 77 for setting data.into the circuitry 74 and display 75.

Figure 8:
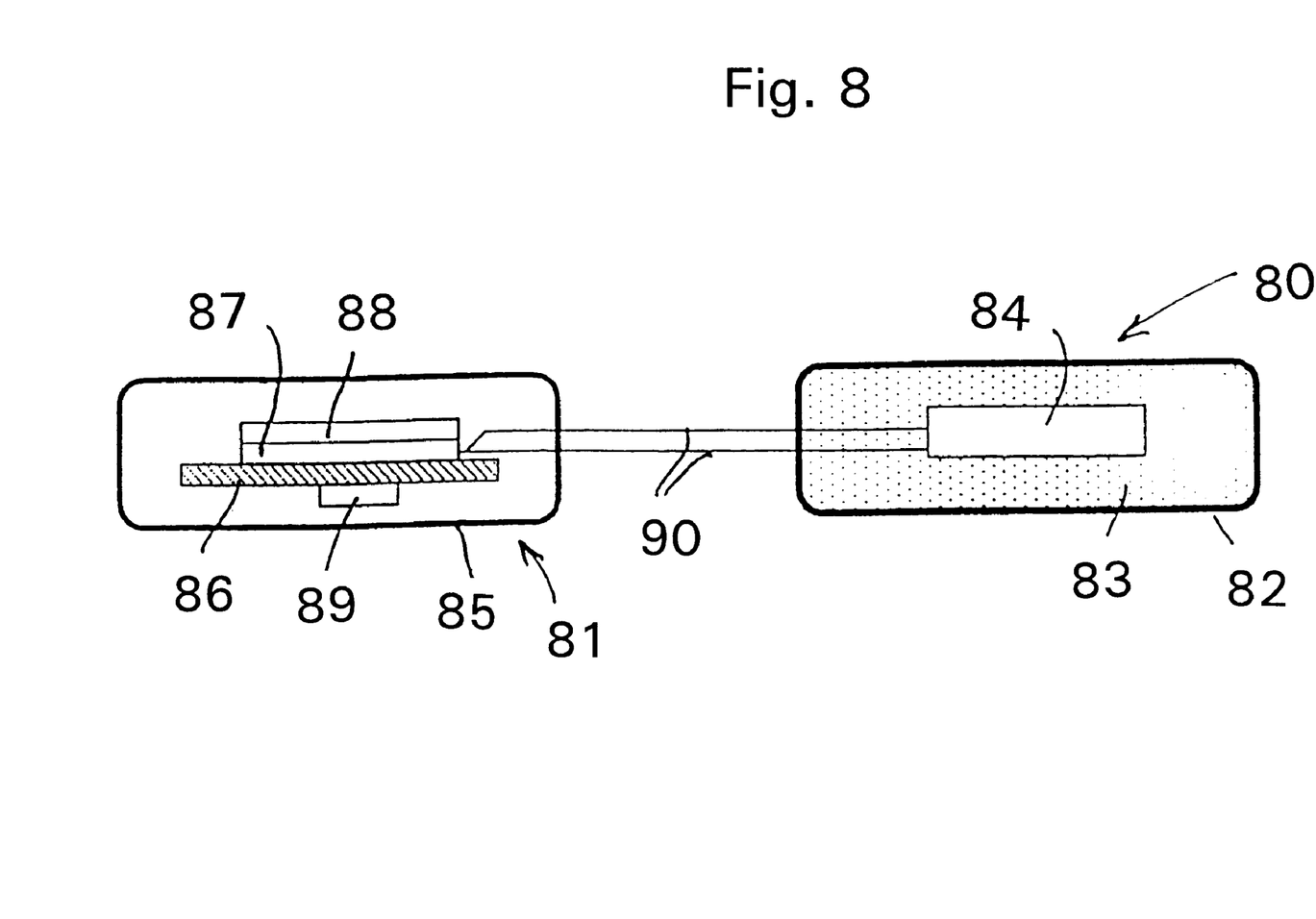
FIG. 8 is illustrative of a form of sensing device according to the invention that may be used as an alternative to that of FIG. 2 in the system of FIG. 1.

Although there is material advantage in providing the electronic circuitry for deriving the measurement data and its transmission and reception, within the same envelope as the mixture or compound and sensing device, this is not necessarily the case. In particular, as illustrated in FIG. 8, a sensing device comprises two capsules 80 and 81, the capsule 80 having a semi-permeable wall 82 and containing the macromolecular mixture or compound 83 and immersed sensor 84. The wall 85 of the capsule 81 on the other hand is non-permeable, and contains components 86 to 89 corresponding directly to the components 16 to 19 respectively of the integrated capsule 11 of FIG. 2. Electrical connection between the sensor 84 and the circuitry 87 is effected by insulated conductors 90.

What is claimed is:

1. A subcutaneous-implant capsule for use in monitoring at least one of presence and activity of a specific chemical analyte, the subcutaneous-implant capsule comprising:

an external wall defining an enclosure for subcutaneous implantation, said wall having at least a portion that is semi-permeable to said chemical analyte;

a macromolecular material contained within the enclosure, said material exhibiting physical change in response to contact with said chemical analyte;

a sensor also contained within the enclosure for providing a response to said physical change in the macromolecular material, and a transmitter for transmitting a signal from said sensor wherein the external wall of the enclosure totally encloses said sensor, said transmitter and the macromolecular material.

2. The subcutaneous-implant capsule according to claim 1 wherein the entire wall of the enclosure is made wholly of semi-permeable membrane.

3. The subcutaneous-implant capsule according to claim 1 further comprising the macromolecular material having a rheological parameter exhibiting a reaction in contact with said chemical analyte wherein the response provided by the sensor is dependent upon the reaction of the rheological parameter.

4. The subcutaneous-implant capsule according to claim 1 wherein the chemical analyte comprises glucose and the macromolecular material exhibits the physical change in contact with glucose.

5. The subcutaneous-implant capsule according to claim 1 wherein said macromolecular material is a mixture of concanavalin A and ficoll.

6. The subcutaneous-implant capsule according to claim 1 wherein said transmitter comprises a device for deriving digital data in accordance with said response of the sensor and for transmitting said digital data from said capsule.

7. The subcutaneous-implant capsule according to claim 1 wherein said transmitter comprises a receiving device for externally-applied adjustment of a datum and a deriving, device for deriving a signal relative to said datum.

8. A sensing system for use in monitoring at least one of presence and activity of a specific chemical analyte, the sensing system comprising:

a bio-compatible implant capsule and interrogating means that is operable for interrogating said capsule, said capsule defining a wall enclosure for bio-compatible implantation, said wall enclosure being at least partially semi-permeable to the specific chemical analyte, a macromolecular material contained within the enclosure, said macromolecular material exhibiting a physical change in response to contact with said specific chemical analyte, a sensor located within the enclosure to respond to said physical change, and a transmitter operable in response to interrogation of said capsule by said interrogating means, the transmitter transmitting to said interrogating means a signal dependent on the response of said sensor, and wherein said wall enclosure totally encloses said sensor, said transmitter and said material.

9. A sensing system according to claim 8 wherein the signal dependent on the response of said sensor is transmitted to said interrogating means by electromagnetic-wave transmission.

10. A sensing system according to claim 8 wherein interrogation of said capsule is effected by electromagnetic-wave transmission from said interrogating means through said wall enclosure of said capsule.

11. A sensing system according to claim 10 wherein electrical power for said transmitter operable in response to interrogation of said capsule, is derived from the electromagnetic-wave interrogating transmission.

12. A sensing system according to claim 8 wherein the chemical analyte comprises glucose and said material exhibits said physical change in response to contact therewith.

13. A sensing system according to claim 8 wherein said material is a mixture of concanavalin A and ficoll.

14. A sensing system according to claim 8 wherein said transmitter includes provision for adjustment of a datum in accordance with data transmitted by the interrogating means, and means for deriving said signal relative to said datum.

15. A sensing device for use in monitoring at least one of presence and activity of a specific chemical analyte, the sensing apparatus comprising:

an enclosure having a membrane-wall that is semipermeable to said chemical analyte, a macromolecular material contained within the enclosure, said macromolecular material exhibiting physical change in response to contact with said chemical analyte, a sensor contained within the enclosure, said sensor being responsive to said physical change exhibited by said macromolecular material to provide an electrical response to said change, and further means contained within the enclosure, said further means being connected within the enclosure to said sensor, and said further means comprising means for deriving a signal dependent on said electrical response of said sensor, and signal-transmitting means for transmitting said signal from within said enclosure to radiate from the sensing device.

16. A sensing device according to claim 15 wherein the signal-transmitting means is means for transmitting said signal by electromagnetic radiation.

17. A sensing system for use in monitoring at least one of presence and activity of a specific chemical analyte, comprising a sensing device and interrogating means that is operable for interrogating said sensing device, said sensing device comprising an enclosure having a membrane-wall that is semi-permeable to said chemical analyte, macromolecular material contained within the enclosure, said material exhibiting physical change in response to contact with said chemical analyte, a sensor contained within the enclosure to respond to said physical change, and further means contained within the enclosure, said further means being connected within said enclosure to said sensor, and said further means being operative in response to interrogation of said sensing means by said interrogating means to transmit to said interrogation means a signal dependent on the response of said sensor to said physical change, said signal being transmitted to said interrogation means by radiation from within the sensing device.

18. A sensing system according to claim 17 wherein the signal dependent on the response of said sensor is transmitted to said interrogating means by electromagnetic-wave transmission.

19. A sensing device for use in monitoring at least one of the presence and activity of a specific chemical analyte, the sensing device comprising:

an enclosure having a membrane-wall that is semi-permeable to said chemical analyte;

a macromolecular material contained within the enclosure, said macromolecular material exhibiting physical change in response to contact with said chemical analyte;

a sensor contained within the enclosure to respond to said physical change of the macromolecular material in response to contact with said chemical analyte, and a transmitter dependent on the response of said sensor for transmitting a signal from said sensing device; and wherein said macromolecular material comprises a material having a rheological parameter exhibiting a change thereof in response to contact with said chemical analyte, and said response of the sensor is dependent upon said change in said rheological parameter.

* * * * *